(12) United States Patent
Mueller-Hartmann et al.

(10) Patent No.: US 7,700,357 B2
(45) Date of Patent: Apr. 20, 2010

(54) METHOD FOR TREATING SMALL VOLUMES WITH ELECTRICAL CURRENT

(75) Inventors: Herbert Mueller-Hartmann, Cologne (DE); Michael Habig, Basel (CH)

(73) Assignee: Lonza Cologne AG (DE)

( * ) Notice: Subject to any disclaimer, the term of this patent is extended or adjusted under 35 U.S.C. 154(b) by 785 days.

(21) Appl. No.: 11/427,474

(22) Filed: Jun. 29, 2006

(65) Prior Publication Data

US 2007/0059834 A1 Mar. 15, 2007

Related U.S. Application Data

(60) Provisional application No. 60/696,806, filed on Jul. 7, 2005.

(30) Foreign Application Priority Data

Jul. 7, 2005 (EP) .................................. 05014758

(51) Int. Cl.
*C12N 15/87* (2006.01)
(52) U.S. Cl. .................................... 435/461; 435/285.2
(58) Field of Classification Search ........................ None
See application file for complete search history.

(56) References Cited

U.S. PATENT DOCUMENTS

| | | | | |
|---|---|---|---|---|
| 5,128,257 | A | * | 7/1992 | Baer ........................ 435/173.6 |
| 5,843,708 | A | * | 12/1998 | Hardman et al. ........... 435/69.1 |
| 5,869,326 | A | | 2/1999 | Hoffman |
| 2004/0014220 | A1 | | 1/2004 | Siebenkotten et al. |
| 2005/0064596 | A1 | | 3/2005 | Rieben et al. |

FOREIGN PATENT DOCUMENTS

WO  WO 2004/110371  12/2004

OTHER PUBLICATIONS

Baum, C. et al. "An Optimized Electroporation Protocol Applicable to a Wide Range of Cell Lines." *Biotechniques*. Dec. 1994, pp. 1058-1062. vol. 17, No. 6. Eaton Publishing.

Beebe, ST. J. et al. "Diverse Effects of Nanosecond Pulsed Electric Fields on Cells and Tissues." *DNA and Cell Biology*. Dec. 2003, pp. 785-796. vol. 22, No. 12. Mary Ann Liebert, Inc.

Poppe, R. et al. "Transfer of plasmid DNA into cells with microelectroporation arrays on a chip," in: "*Microreaction Technology: Industrial Prospects.*" *IMRET 3: Proceedings of the Third International Conference on Microreaction Technology*. Apr. 1999, pp. 461-468. Springer Publishings (Ehrfeld (Ed.)).

Gehl, J. et al. "Electroporation: theory and methods, perspectives for drug delivery, gene therapy and research." *Acta Physiologica Scandinavica*. 2003, pp. 437-447. vol. 177, No. 4 Blackwell Publishing.

Lakshmi, P. et al. "Construction of a Low Cost and Simple Electroporator for High Transformation Efficiencies in *E. Coli* strains." *The Chemical Engineering and Biochemcial Engineering Journal* (1994) B75-B77. vol. 56. Elsevier Science S.A.

* cited by examiner

*Primary Examiner*—James S Ketter
(74) *Attorney, Agent, or Firm*—Joyce von Natzmer; Pequignot + Myers LLC

(57) ABSTRACT

Disclosed is a method for treating biological material via electrical current, in which the biological material is added to a small volume of a buffer solution having relative high ionic strength. A strong electrical field is generated in the buffer solution by a high voltage pulse having a preset duration.

The biological material is added to at most 50 μl of a buffer solution with an ionic strength of at least 100 mmol/l. By at least one voltage pulse having a preset duration of at least 10 μs, an electrical field with a field strength of at least 1 kV/cm is generated in the buffer solution. The voltage pulse is hereby interrupted at least once for a duration of at least 100 μs and is then again continued.

15 Claims, 5 Drawing Sheets

METHOD FOR TREATING SMALL VOLUMES WITH ELECTRICAL CURRENT

CROSS REFERENCE TO RELATED APPLICATIONS

This application claims the benefit of U.S. provisional application 60/696,806, and claims priority to European application EP05014758.6, both filed Jul. 7, 2005, U.S. provisional application 60/696,806 is incorporated herein by reference in its entirety.

FIELD OF THE INVENTION

The invention relates to a method for treating biological material using electrical current. In particular, biological material is added to a small volume of a buffer solution having relative high ionic strength and, in this buffer solution, a strong electrical field is generated for a preset duration via a high voltage pulse.

BACKGROUND

The introduction of biologically active molecules, such as for example DNA, RNA or proteins, into living cells is an important tool for the analysis of biological functions of these molecules. A preferred method for the introduction of foreign molecules into cells is electroporation which, in contrast to chemical methods, does not depend on the simultaneous transport of other biologically active molecules. In electroporation, the foreign molecules are introduced into the cells from a buffer solution adapted to the cells or from a cell culture medium via a brief current flow. The cell membrane is being made permeable to the foreign molecules by the action of the short electrical pulses. In addition, the cell suspension is frequently located in a so-called cuvette, i.e. a narrow vessel that is open at the top, and whose interior is formed by two pairs of side walls arranged parallel and opposite to one another.

The interior can receive the cell suspension, i.e. generally an aqueous buffer solution or a cell culture medium, in which the cells to be treated are suspended. Such cuvettes generally have a pair of electrodes in the lower region of a pair of opposing side walls, which allow for the application of an electric voltage. An electrical discharge at these electrodes results in an electrical current flowing between the electrodes and through the cell suspension, causing nucleic acids or other molecules to be transported into the cells or leading, depending on the conditions selected, to cell fusion.

As a result of the brief application of a strong electrical field, i.e. a short pulse with high current density, cells, cell derivatives, sub-cellular particles and/or vesicles can also be fused. In this so-called electrofusion, the cells are at first brought into close membrane contact, for example via an inhomogeneous electrical alternating field. The subsequent application of an electric field pulse results in the interaction of membrane parts which eventually leads to fusion. For electrofusion, apparatuses may be used which are comparable to those used for electroporation.

During electroporation, the biologically active molecules initially enter the cytoplasm through the temporarily produced 'pores' in the cell membrane. In certain cases, the molecules may already perform the function of interest in the cytoplasm and, subsequently, under certain conditions, may also enter the nucleus. In particular with applications in which the biologically active molecules can only carry out the function of interest in the nucleus, for example, if the expression of a gene is to be analysed, and, in particular, if cells without, or with only low, division rates are used, for example primary cells, it is advantageous if the biologically active molecules are transported directly into the nucleus.

It is known from the electroporation method disclosed in US2004014220, which is incorporated herein by reference in its entirety, that in such cases, to achieve high transfection efficiency, a strong electrical field having a field strength of at least 2 kV/cm has to be generated in the buffer solution for a preset duration of at least 10 µs via a high voltage pulse.

A method for treating biological material by means of high electrical currents is also known from US2005064596, which is incorporated herein by reference in its entirety. In the method disclosed therein, the biological material is added to a buffer solution having an ionic strength of at least 200 mmol/l to ensure a low cell mortality rate while accomplishing high transfection efficiency.

Primarily in biochemical and pharmaceutical applications, in which a plurality of reaction batches have to be tested simultaneously and in the shortest possible time, in particular in HT analyses (HT=high throughput), it is necessary to provide as large a number of reaction chambers as possible, for example 96 or 384. The reaction vessels used in this context are generally referred to as multi well plates, microtitration plates or multi wells. The individual reaction chambers ('wells') of these vessels are relatively small and can therefore only receive small volumes. Moreover, it is frequently advantageous to use smaller sample volumes to save buffer and cell material. In addition, in particular with valuable cell material, for example primary cells, only small amounts of cells are generally available. It is therefore frequently desirable and in certain instances necessary to work with small sample volumes.

Electrical hydrolysis cannot be excluded as a side effect when generating strong electrical fields in liquids. In the mildest case, electrolysis can be noticed by the formation of gas bubbles on the surfaces of the electrodes, which in turn leads to the formation of foam. In an extreme case, explosion-type gas formation occurs, which due to the resulting displacement effect, leads to the expulsion of the samples from the area between the electrodes (referred to hereinafter as 'spattering'). The latter generally results in the loss of sample (s) or at least in the sample not remaining in the electrical field for the time intended. The spattering of a sample therefore qualitatively and/or quantitatively impairs the result of a test or sample processing and moreover has a negative effect on the reproducibility of the results. Accordingly, in the various applications where treatment of biological cells in electrical fields is necessary, in particular during electroporation, electrolysis constitutes an undesirable side effect.

In theory, the probability of spattering could be reduced by reducing the electrical conductivity. Higher cells which are not provided with rigid cell walls, however, can generally only survive in solutions with a specific osmolarity. Generally, electrolytes are also amongst the osmotically effective dissolved substances which result in a more or less high electrical conductivity of the solution. For example, to carry out electroporation, it is generally necessary to introduce ions into the cell suspension and, as disclosed in US2005064596, which is incorporated herein by reference in its entirety, also advantageous. Thus, for practical reasons, there are limits to reducing the probability of spattering by reducing the electrical conductivity. Accordingly, in such cases electrolysis of varying degrees can be expected.

The occurrence of spattering is hereby a stochastic event. This means that the event can only be described by probabilities. Depending on the prescribed conditions, the frequency of undesired spattering may, for example, be under 5%, but can also be over 95%. The probability of spattering is, hereby particularly high when low volumes are used at a high current density. In order to develop a process to the production stage, the problem poses itself to reduce this probability by appropriate methods, which are to be employed by the customer to under 1%, for example.

Thus, there is a need in the art to provide a method of the aforementioned type in which the frequency of the undesired expulsion of a sample from the area between the electrodes is significantly reduced.

SUMMARY OF THE INVENTION

In one embodiment, the invention provides a method in which biological material is added to at most about 50 µl of a buffer solution having an ionic strength of at least about 100 mmol/l and in which an electrical field with a field strength of at least about 1 kV/cm is generated for a preset duration of at least 10 µs via at least one voltage pulse. The voltage pulse may be interrupted at least once for a duration of at least about 100 µs and is subsequently continued. The preset duration of the voltage pulse corresponds hereby to the de facto duration of the pulse without interruptions, i.e. to the total net time in which current actually flows. Thus, as a result of the additional time periods when the voltage pulse is interrupted, the total duration of the pulse increases accordingly, so that the voltage pulse from its release to its conclusion, i.e. until reaching the preset duration, is actually longer than the preset duration. In the method according to the invention, the voltage pulse is interrupted after a predetermined time for the predetermined durations and subsequently continued. This process is repeated as often as required to reach the preset duration of the voltage pulse. The voltage pulse thereby has to be interrupted sufficiently frequently that the generation of gas in the buffer solution is sufficiently reduced to prevent expulsion of the sample from the area between the electrodes. Moreover, the durations of the individual interruptions have to be sufficiently long to prevent expulsion of the sample from the area between the electrodes. Thus, by interrupting the voltage pulse, the spattering frequency can be markedly reduced under otherwise prescribed conditions while the efficiency of the method in use, in particular the transfection efficiency, is maintained.

The frequency of undesired spattering is positively dependent, on the one hand, for example during electroporation, on the current density (field strength×specific electrical conductivity) and the time interval during which the electrical field is applied. The current density and time interval are hereby directly related to the amount of gas produced by electrolysis per sample volume. The field strength and the time interval determine the conditions under which, for example, high transfection efficiency or direct transport of the molecules into the nucleus may be achieved. A reduction of one of these two parameters away from the optimal cell type-specific conditions generally leads to a qualitative and/or quantitative decline of the test results. Thus, reducing one of these parameters is not possible or only possible to a limited extent. On the other hand, the spattering probability is negatively dependent on the volume of the sample (mass). This dependency results from the greater inertness of a larger volume. Within the short time window, it is more likely that larger volumes remain in the cuvette gap. Thus with small volumes, in otherwise equivalent conditions, spattering results particularly frequently. The spattering problem therefore plays a particular role with methods in the HT field. However, for particular applications, in particular in the high throughput area, the volume of a sample cannot be increased. On the one hand, a larger number of samples with increasing volumes cannot be handled by automatic liquid handling systems, or only with increased cost, and on the other hand, the amount of cell material available (and possibly reagent) is often restricted in view of the costs associated with it. Moreover, the use of a large volume may also be disadvantageous for other reasons. A reduction of the cell concentration leads, from a certain point onwards, to noticeably worse results, for example with regard to the cell survival rate during electroporation or with regard to the efficiency during electrofusion. Thus, in particular with HT methods, there is an increase in volume is not really an option. Thus, the method according to the invention, allows, effectively and reliably, for a noticeable reduction in the frequency of spattering under otherwise predetermined conditions.

In an advantageous embodiment of the invention the voltage pulse is interrupted twice to ten times, including three, four, five, six, seven, eight and/or nine times. The number of interruptions hereby depends on the preset conditions, in particular the current density, the duration of the pulse and the volume available. The optimal number of interruptions frequently has to be empirically determined for the respective application and/or the cell type used. Such an empirical determination is, however, well within the abilities of the skilled artisan.

According to the invention, for at least one interruption a duration of about 200 µs to about 2 ms, preferably about 300 µs, about 400 µs, about 500 µs, about 600 µs, about 700 µs, about 800 µs, about 900 µs, about 1 ms or about 1.5 ms may be preset. As long as the interruption intervals do not exceed a certain length, the spattering of the sample may be prevented without this having negative effects on the quality of the results of the method. The optimal interruption duration and/or the interruptions, respectively must therefore generally be empirically determined for the respective application and/or the cell type used. Such an empirical determination is, however, well within the abilities of the skilled artisan. The duration required for the reduction of the probability of spattering, further depends in particular on the preset conditions, i.e. the current density, the duration of the pulse and the volume available.

The volume of the buffer solution with the biological material may, for example, be in total between about 1 and about 50 µl, preferably about 10 to about 40 µl, particularly preferably about 15 to about 25 µl, in particular about 10 to about 20 µl. Moreover, the volume used generally depends on the availability of the biological material and/or the chemical engineering conditions.

In another advantageous embodiment of the invention, the voltage pulse generates an electrical field with a field strength having a maximally about 10 kV/cm, preferably about 1 to about 8 kV/cm, particularly preferably about 2 to about 6 kV/cm, in particular about 2 to about 4 kV/cm. Such high voltage pulses are particularly suitable for the electroporation of eukaryotic cells, in particular the introduction of nucleic acids into the nucleus.

In a further advantageous embodiment of the invention, the voltage pulse has a preset duration having a maximum of about 5 ms, preferably about 20 µs to about 2 ms, particularly preferably about 100 to about 1000 µs, in particular about 100 to about 600 µs. The preset duration is thereby the predetermined length of the voltage pulse without interruptions, i.e. the time period in which current is actually applied and current flows, respectively. The preset duration is generally an empirically determined value, which is optimal for the respective application and/or the cell type used. In particular, applications in which slightly reduced efficiencies are expected because of the interruptions to the voltage pulse provided by the method according to the invention, these reduced efficiencies may, in certain cases, be improved by, for example, extending the preset duration within certain limits beyond the empirically determined value. In this manner, it is possible to compensate in individual cases for the possible negative effects of interrupting the voltage pulse.

In an advantageous embodiment of the invention, it is further provided that the voltage pulse is interrupted approximately after a voltage interval of about 5 μs, about 10 μs, about 20 μs, about 30 μs, about 40 μs, about 50 μs, about 60 μs, about 100 μs or about 200 μs. This may apply to the first voltage interval or one or more of the subsequent voltage intervals. A voltage interval is therefore a time period in which voltage is applied and an electrical field is generated in the buffer solution, respectively and which is followed by an interruption interval or which is preceded by an interruption interval. Under certain conditions, by shortening one or more voltage intervals, the probability of spattering may be further reduced and/or minimised.

According to the invention, the electrical field may be generated between two electrodes. The distance between the two electrodes can, in a particularly advantageous embodiment of the invention, be about 0.5 to about 5 mm, preferably about 1 to about 4 mm, in particular about 1.5 to about 2 mm. In any case, the distance between the electrodes has to be dimensioned according to the geometry of the reaction container used, such that the volume of buffer solution available may sufficiently wet the area between the electrodes.

In an advantageous embodiment of the invention it is further provided that the treatment of the biological material is carried out in a reaction container which has a substantially square, rectangular or round cross-section. In addition, the reaction container may have a substantially rectangular reaction chamber which is delimited laterally by two electrodes having a plane-parallel configuration.

The invention is described in more detail below with reference to the Figures by way of example.

DETAILED DESCRIPTION OF VARIOUS AND PREFERRED EMBODIMENTS

Figure 1:
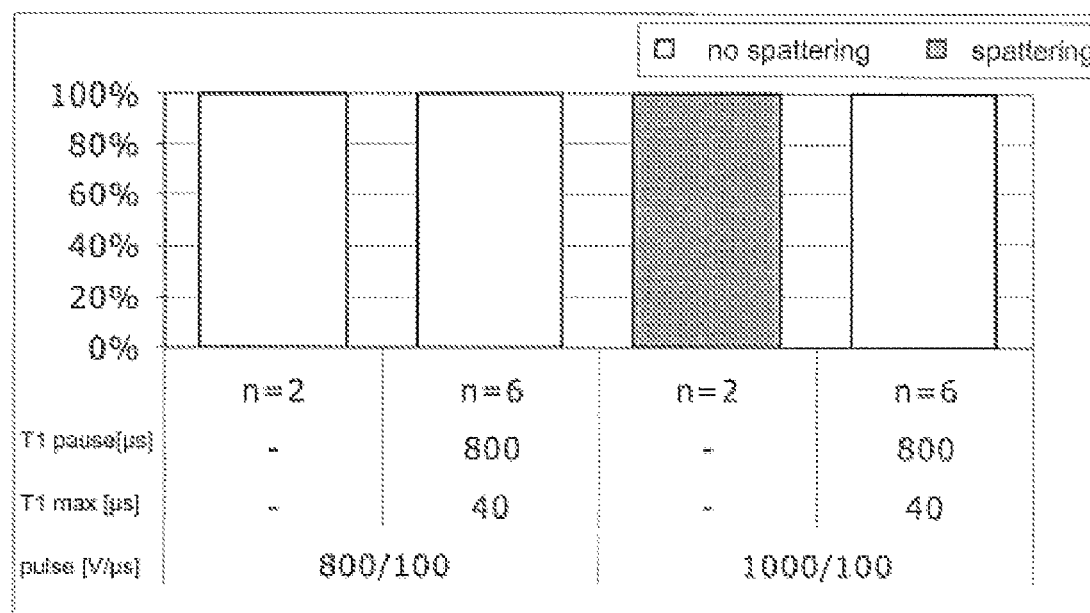
FIG. 1 is a bar chart of the spattering frequency depending on the voltage, high-throughput Nucleofector® (HT-beta, Amaxa GmbH), volumes of cell suspension: 20 μl, gap width of the cuvette: 1.5 mm, ionic strength of the buffer solution: 203 mmol/l (electrical conductivity: 11.3 mS/cm), the black shaded area shows the spattering frequency of the individual samples, n=number of samples.

FIG. 1 shows a bar chart of the spattering frequency depending on the voltage in the form of a comparison of two different voltage pulses, which were carried out respectively with and without interruption. The first voltage pulse has a preset duration of 100 μs at an externally applied voltage of 800 V. This provides for a field strength of approximately 4 kV/cm which can be calculated from the voltage and the electrode resistance. The second voltage pulse also has a preset duration of 100 μs but with an applied voltage of 1000 V, a field strength of approximately 5 kV/cm can be calculated from the voltage. The two voltage pulses were respectively interrupted twice after 40 μs (T1 max), i.e. the pulse was interrupted after 40 μs, then continued, after a further 40 μs again interrupted and finally completed with a voltage interval of 20 μs, so that a total preset duration of 100 μs was reached. The durations of the interruptions were respectively 800 μs (T1 pause). As a whole, each voltage pulse therefore is made up of 3 voltage intervals and 2 interruption intervals, the entire duration of the pulses adding up to a total of 1700 μs. It is clear here that applying the voltage pulse with the lower voltage and/or field strength under the preset conditions does not result in expulsion of the samples, i.e. in this case it does not spatter. In contrast, the voltage pulse at the higher voltage and/or field strength leads to expulsion of the samples (third bar). This undesirable spattering may be prevented by interrupting the voltage pulse twice (last bar). It therefore shows, on the one hand, that the spattering probability under otherwise constant conditions becomes higher with increasing field strength, and on the other hand, that an expulsion of the sample from the reaction container, even at very high field strengths, may be prevented by interrupting the voltage pulse. At least by interrupting the pulse the probability of spattering is significantly reduced.

Figure 2:
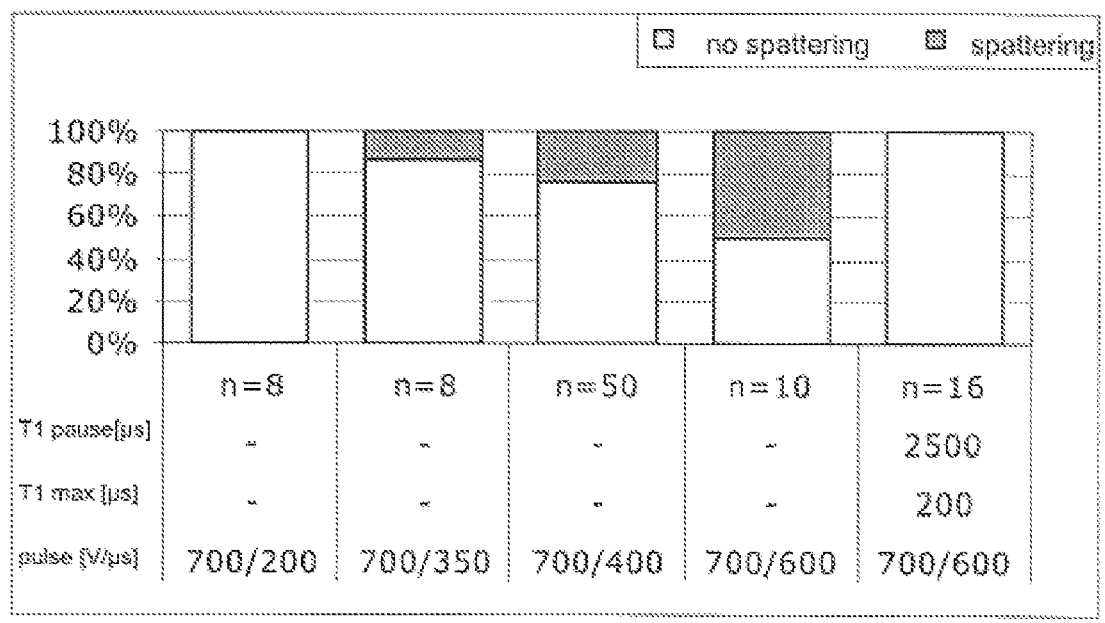
FIG. 2 is a bar chart of the spattering frequency depending on the pulse duration, high throughput Nucleofector® (HT-beta, Amaxa GmbH), volumes of the cell suspension: 20 μl, gap width of the cuvette: 1.5 mm, ionic strength of the buffer solution: 129 mmol/l (electrical conductivity 7.2 mS/cm), the black shaded area shows the spattering frequency of the individual samples, n=number of samples.

FIG. 2 shows a bar chart of the spattering frequency depending on the pulse duration, whereby voltage pulses were used with a strength of respectively 700 V (3.5 kV/cm field strength), with increasing preset duration of 200, 350, 400 and 600 μs. It was shown that the percentage frequency of spattering increases with increasing pulse duration. Interrupting the voltage pulse according to the invention with the longest preset duration of 600 μs the spattering of the samples could however be effectively prevented. The voltage pulses were, to this end, respectively interrupted twice after 200 μs (T1 max), i.e. the pulse was interrupted after 200 us then continued, after a further 200 μs again interrupted and finally completed with a voltage interval of 200 μs again, so that a total preset duration of 600 us was achieved. The interruption durations were respectively 2.5 ms (T1 pause). In total, each voltage pulse is made up of 3 voltage intervals and 2 interruption intervals, the total duration of the pulse adding up to a total of 5.6 ms. This makes clear that with a relatively long preset duration of the voltage pulse there is a high probability that it leads to expulsion of the samples (fourth bar). This undesired spattering may be prevented by interrupting the voltage pulse twice (last bar). Thus, on the one hand, it is shown that the probability of spattering under otherwise constant conditions becomes higher with increasing pulse duration and, on the other hand, that an expulsion of the sample from the reaction vessel may be prevented even with a relatively long preset duration by interrupting the voltage pulse.

Figure 3:
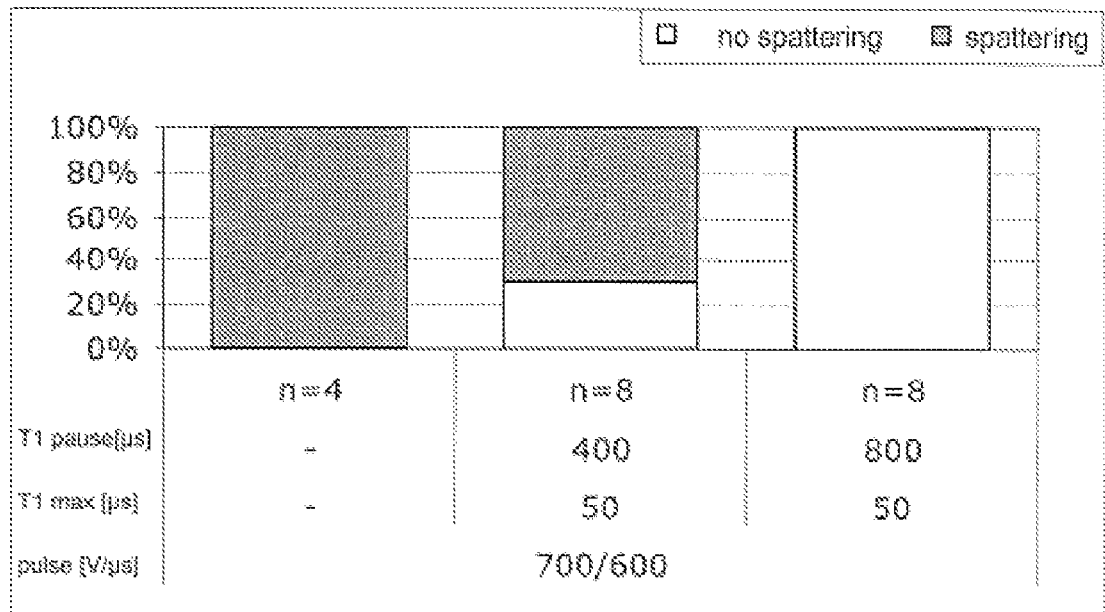
FIG. 3 is a bar chart of the spattering frequency depending on the interruption duration of the voltage pulse, high throughput Nucleofector® (HT-beta, Amaxa GmbH), volumes of the cell suspension: 20 μl, gap width of the cuvette: 1.5 mm, ionic strength of the buffer solution: 203 mmol/l (electrical conductivity 11.3 mS/cm), the black shaded area shows the spattering frequency of the individual samples, n=number of samples.

FIG. 3 shows a bar chart of the spattering frequency depending on the durations of the interruption of the voltage pulse. It is clear that in this example that at least for specific applications and/or conditions by extending the durations of the interruption(s) the probability of the expulsion of the sample may be further reduced. A voltage pulse with a voltage of 700 V (3.5 kV/cm field strength) and a preset duration of 600 μs was used uninterrupted (first bar), interrupted 11× for every 400 μs (second bar) or interrupted 11× for every 800 μs (third bar). The interrupted pulses therefore are made up of 12 voltage intervals of respectively 50 μs in length (T1 max) and 11 interruption intervals of respectively 400 μs or 800 μs (T1 pause). If the voltage pulse is not interrupted according to the invention under these conditions, spattering occurs at each test and/or each sample. Whilst spattering occurs at an interruption duration of 400 μs, for approximately 70% of the samples, the spattering however may be completely prevented under these conditions by doubling the interruption durations. Naturally, the relationship between the substances in the buffer solution 'calms down' with the increasing length of interruption(s) so that, during the voltage interval following the interruption, gas is no longer formed in the sample.

Figure 4:
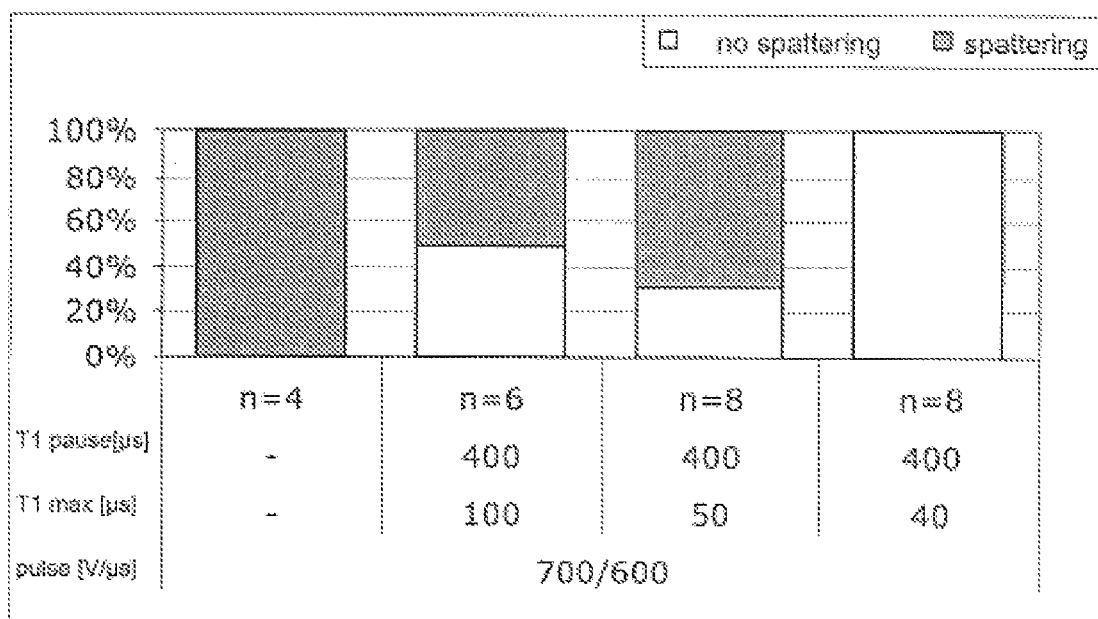
FIG. 4 is a bar chart of the spattering frequency depending on the maximum duration of an uninterrupted voltage interval, high throughput Nucleofector® (HT-beta, Amaxa GmbH), volumes of the cell suspension: 20 μl, gap width of the cuvette: 1.5 mm, ionic strength of the buffer solution: 203 mmol/l (electrical conductivity 11.3 mS/cm), the black shaded area shows the spattering frequency of the individual samples, n=number of samples.

FIG. 4 shows a bar chart of the spattering frequency depending on the maximum duration of an uninterrupted voltage interval. This test was carried out practically under the same conditions as the test according to FIG. 3, with the difference that the interruption durations (T1 pause) were maintained constant at 400 μs, whilst the maximum length of the voltage intervals (T1 max) i.e. the durations in which the electrical field is generated was varied. When comparing the tests with T1 max=100 μs and T1 max=40 μs, it is clear that a shortening of the voltage interval i.e. the time until the voltage pulse is interrupted, leads to a reduction of the probability of spattering. Moreover, in the present embodiment several factors indicate here that a threshold value between 40 and 50 μs exists, i.e. in this case there is no proportional dependency of the spattering frequency on T1 max.

Figure 5:
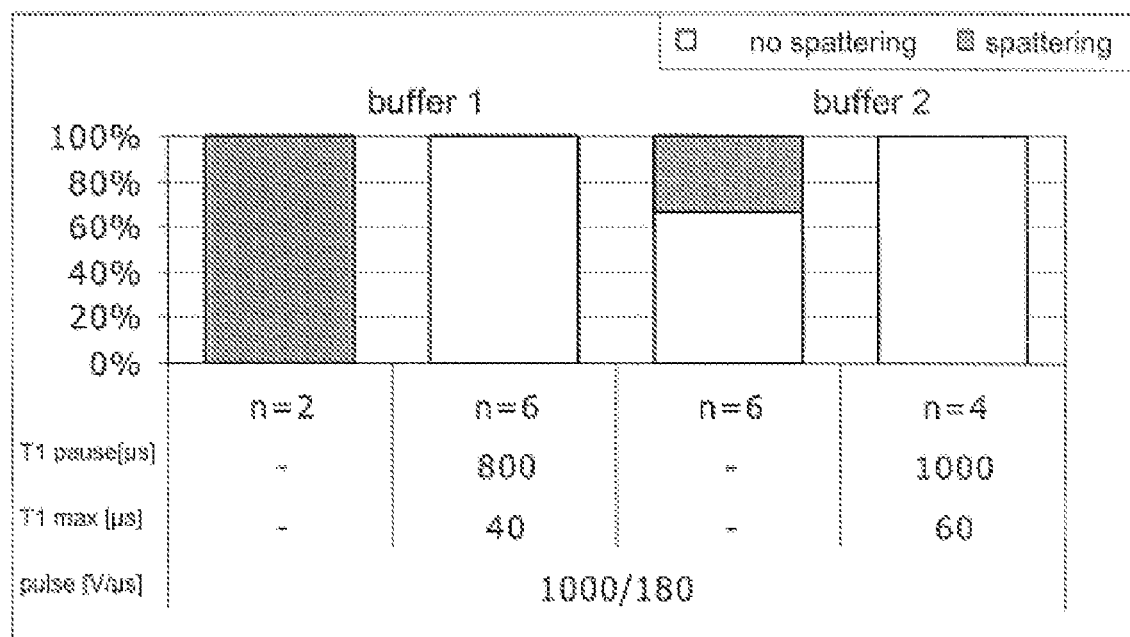
FIG. 5 is a bar chart of the spattering frequency depending on the electrical conductivity and/or ionic strength of the buffer solution, high throughput Nucleofector® (HT-beta, Amaxa GmbH), volumes of the cell suspension: 20 μl, gap width of the cuvette: 1.5 mm, ionic strength of the buffer solution:), the black shaded area shows the spattering frequency of the individual samples, n=number of samples, buffer 1: ionic strength 203 mmol/l and electrical conductivity 11.3 mS/cm, buffer 2: ionic strength 129 mmol/l and electrical conductivity 7.2 mS/cm.

FIG. 5 shows a bar chart of the spattering frequency depending on the electrical conductivity and/or ionic strength of the buffer solution. When using a buffer with higher ionic strength (buffer 1: ionic strength 203 mmol/l and electrical conductivity 11.3 mS/cm) the risk of spattering is substantially greater than when using a buffer with lower ionic strength (buffer 2: ionic strength 129 mmol/l and electrical conductivity 7.2 mS/cm). In both examples shown, the spattering may, however, be prevented by the interruption of the voltage pulse according to the invention.

Figure 6:
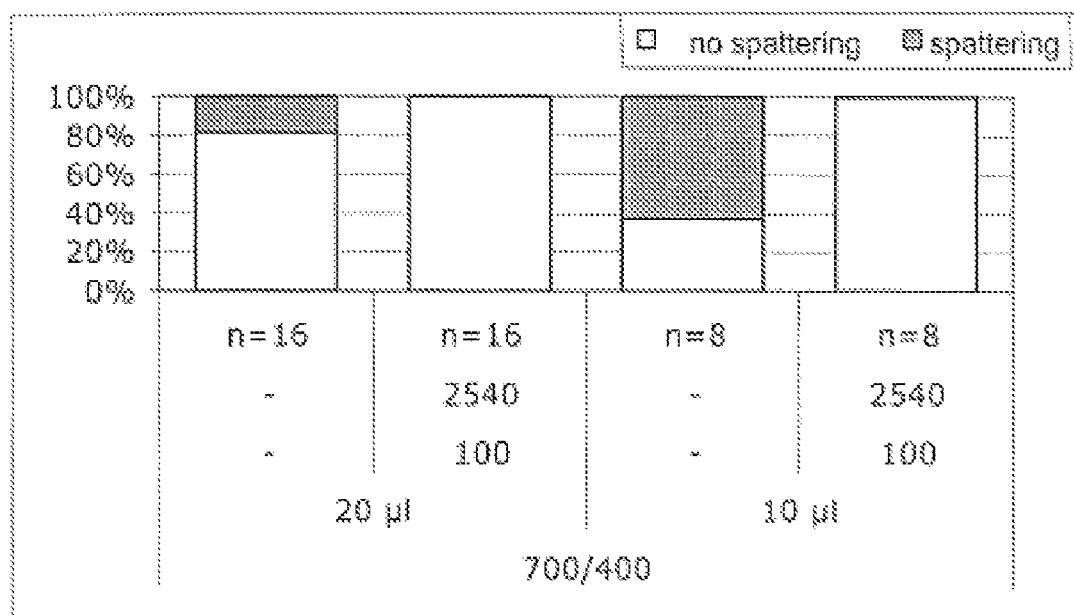
FIG. 6 is a bar chart of the spattering frequency depending on the volume of the cell suspension, high throughput Nucleofector® (HT-beta, Amaxa GmbH), gap width of the cuvette: 1.5 mm, ionic strength of the buffer solution: 129 mmol/l (electrical conductivity 7.2 mS/cm), the black shaded area shows the spattering of the individual samples, n=number of samples.
Figure 7:
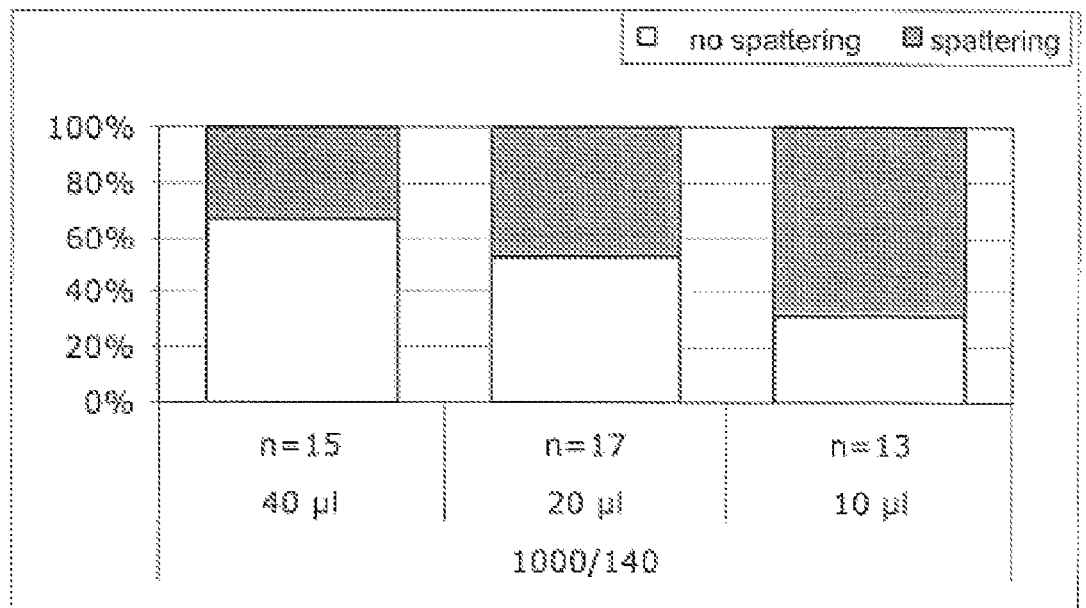
FIG. 7 is a bar chart of the spattering frequency depending on the volume of the cell suspension, high throughput Nucleofector® (HT-beta, Amaxa GmbH), gap width of the cuvette: 1.5 mm, ionic strength of the buffer solution: 203 mmol/l (electrical conductivity 11.3 mS/cm), the black shaded area shows the spattering frequency of the individual samples, n=number of samples.

FIGS. 6 and 7 show respectively a bar chart of the spattering frequency depending on the volume of the cell suspension. From both illustrations it is clear that the probability of spattering is higher, the lower the volume of the cell suspension and/or buffer solution. In this connection, the example according to FIG. 6 shows that, even in applications where only very low volumes may be used, the spattering probability may practically be reduced to zero.

Figure 8:
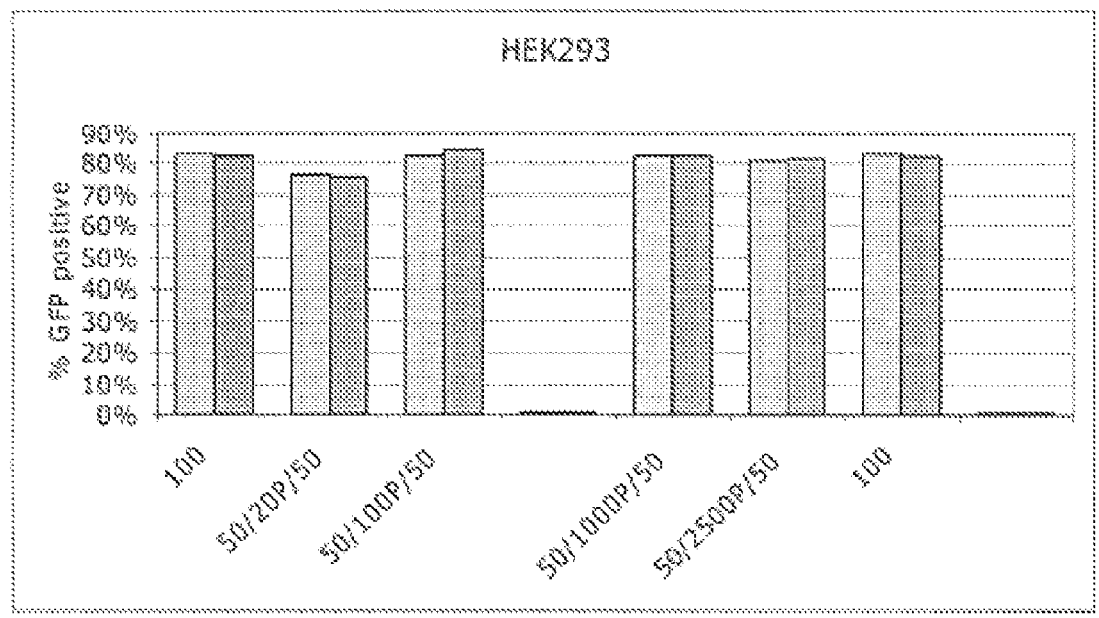
FIG. 8 is a bar chart of the transfection efficiency depending on the interruption duration of the voltage pulse, high throughput Nucleofector® (HT beta, Amaxa GmbH), gap width of the cuvette: 1.5 mm, ionic strength of the buffer solution: 203 mmol/l (electrical conductivity 11.3 mS/cm), for detecting the transfection efficiency respectively $2\times10^5$ HEK293 cells are received in 20 μl buffer solution, with 0.1 μg pEGFP-C1 (Invitrogen) added and exposed to a field of 4 kV/cm, then the cells were received in Minimum Essential Medium Eagle (ATCC) with 100 μg/ml streptomycin, 100 U/ml penicillin and 10% horse serum (ATCC) and cultivated in a humidified incubator for 24 hours at 37° C. and 5% $CO_2$, finally the samples were tested for GFP expression, by means of flow cytometry (FACSCalibur, Becton Dickinson), the respective double values of the percentage of the GFP expressing cells are shown, the bar chart text relates to the interruption of the field exposure; all data are in μs, the numbers at the start and the end represent the duration of the uninterrupted voltage intervals, the numbers between the horizontal lines representing the interruption duration there between (P=pause)
Figure 9:
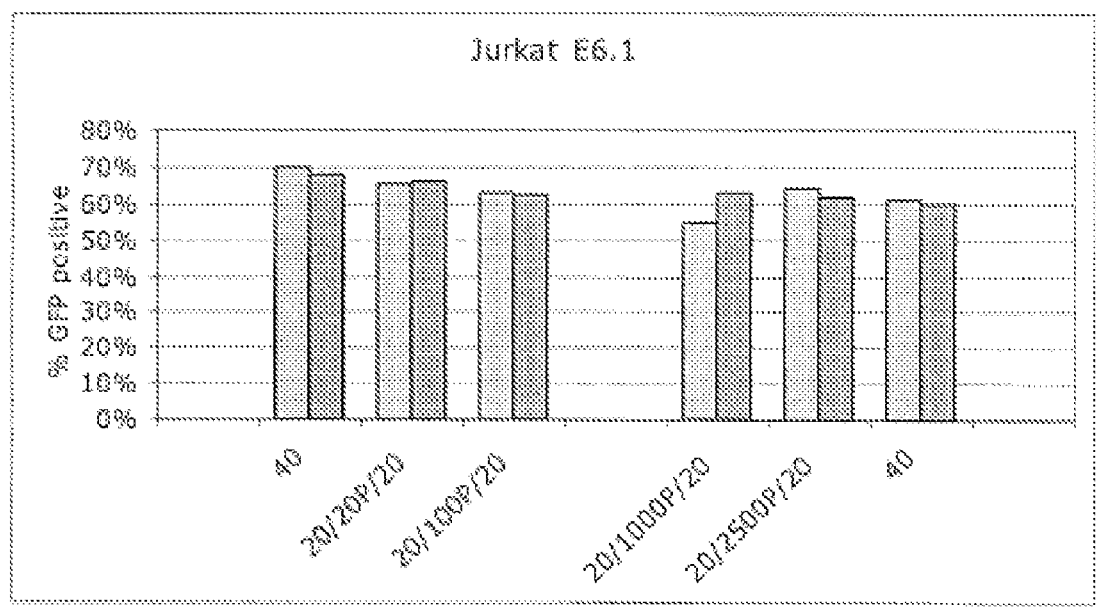
FIG. 9 is a bar chart of the transfection efficiency depending on the interruption duration of the voltage pulse, high throughput Nucleofector® (HT-beta, Amaxa GmbH), gap width of the cuvette: 1.5 mm, ionic strength of the buffer solution: 203 mmol/l (electrical conductivity 11.3 mS/cm), for the detection of the transfection efficiency respectively $2\times10^5$ jurkat E6.1 cells are received in 20 μl buffer solution with 1 μg pmaxGFP (Amaxa) added and exposed to a field of 1.25 kV/cm, then the cells were received in RPMI-1640 medium (ATCC) with 100 μg/ml streptomycin, 100 U/ml penicillin and 10% FCS (ATCC) and cultivated for 24 hours at 37° C. at 5% $CO_2$ in a humidified incubator, finally the samples were examined for GFP expression by means of flow cytometry (FACSCalibur, Becton Dickinson), the respective double values of the percentage of the GFP expressing cells are shown, the bar chart text relates to the interruption to the field exposure: all data are in μs, the numbers at the start and the end represent the duration of the uninterrupted voltage intervals, the numbers between the horizontal lines representing the interruption duration there between (P=pause).

FIGS. 8 and 9 respectively show a bar chart of the transfection efficiency depending on the interruption duration of the voltage pulse. The transfection efficiency is surprisingly not negatively affected by the interruption of the voltage pulse according to the invention. The efficiency of the method is always approximately at the same high level, irrespective of whether the voltage pulse is interrupted (double bars 2 to 5) or not (double bars 1 and 6).

As a whole it is therefore shown that under otherwise prescribed conditions (field strength and/or current density, preset duration of the voltage pulse, volume of buffer solution) a voltage interval may not exceed a specific uninterrupted length, in order to prevent sufficiently the occurrence of spattering and/or the probability of expulsion of the sample from the reaction vessel. Thus the spattering problem under otherwise preset conditions can be solved by the pulse being interrupted and/or a voltage interval not exceeding a critical uninterrupted length. Therefore, the interruption of the voltage pulse leads to a marked reduction of the spattering probability, without the quality of the method, in this case in particular the transfection efficiency, being impaired.

Once given the above, non-limiting disclosure, many other features, modifications, and improvements will become apparent to the skilled artisan. Such other features, modifications, and improvements are therefore considered to be part of this invention, the scope of which is to be determined by the following claims:

We claim:

1. A method for treating biological material by means of an electrical current comprising
    providing no more than about 50 μl of a buffer solution having an ionic strength of at least about 100 mmol/l,
    adding the biological material to said buffer solution,
    applying, for a preset duration of at least about 10 μs, at least one voltage pulse to said buffer solution to generate an electrical field having a field strength of at least about 1 kV/cm, wherein the voltage pulse is interrupted at least once for a duration of at least about 100 μs and is subsequently continued.

2. The method of claim 1, wherein said voltage pulse is interrupted twice to ten times.

3. The method of claim 1 or 2, wherein a duration of about 200 μs to about 2 ms is preset for at least one interruption of said voltage pulse.

4. The method of claim 3, wherein the duration is about 300 μs, about 400 μs, about 500 μs, about 600 μs, about 700 μs, about 800 μs, about 900 μs, about 1 ms or about 1.5 ms.

5. The method of claim 1, wherein the buffer solution including the biological material has a total volume of between about 1 and about 50 μl.

6. The method of claim 5, wherein said volume is between about 10 and about 40 μl, between about 15 and about 25 μl or between about 10 to about 20 μl.

7. The method of claim 1, wherein said voltage pulse generates an electrical field with a field strength having maximally about 10 kV/cm.

8. The method of claim 7, wherein the field strength is about 1 to about 8 kV/cm, about 2 to about 6 kV/cm or about 2 to about 4 kV/cm.

9. The method of claim 1, wherein the voltage pulse has a preset duration having a maximum of about 5 ms.

10. The method of claim 9, wherein said preset duration is about 20 μs to about 2 ms, about 100 to about 1000 μs or about 100 to about 600 μs.

11. The method of claim 1, wherein the voltage pulse is interrupted after a voltage interval of about 5 μs, about 10 μs, about 20 μs, about 30 μs, about 40 μs, about 50 μs, about 60 μs, about 100 μs or about 200 μs.

12. The method of claim 1, wherein the electrical field is generated between two electrodes and wherein the distance between the two electrodes is about 0.5 to about 5 mm.

13. The method of claim 12, wherein said distance is about 1 to about 4 mm or about 1.5 to about 2 mm.

14. The method of claim 1, wherein the biological material is treated in a reaction container, which has a substantially square, rectangular or round cross-section.

15. The method of claim 9, wherein the reaction container has a substantially rectangular reaction chamber, which is delimited laterally by two electrodes having a plane-parallel configuration.

* * * * *